United States Patent [19]

Hood

[11] Patent Number: 5,536,715
[45] Date of Patent: Jul. 16, 1996

[54] COMBINATIONS OF ANTHELMINTICALLY ACTIVE AGENTS

[75] Inventor: John D. Hood, Betchworth, England

[73] Assignee: Pfizer Inc., New York, N.Y.

[21] Appl. No.: 457,734

[22] Filed: Jun. 1, 1995

Related U.S. Application Data

[63] Continuation of Ser. No. 64,014, filed as PCT/GB91/01982 Jan. 1, 1994, published as WO92/08468 May 29, 1992, abandoned.

[30] Foreign Application Priority Data

Nov. 16, 1990 [GB] United Kingdom ............... 9024924

[51] Int. Cl.$^6$ ............... A61K 31/55; A61K 31/54; A61K 31/535; A61K 31/53
[52] U.S. Cl. ............... 514/211; 514/214; 514/222.2; 514/222.5; 514/223.8; 514/226.8; 514/228.2; 514/228.8; 514/229.2; 514/233.2; 514/241; 514/242; 514/244; 514/250; 514/450
[58] Field of Search ............... 514/211, 214, 514/222.2, 222.5, 223.8, 226.8, 228.2, 228.8, 229.2, 233.2, 241, 242, 244, 250, 450

[56] References Cited

U.S. PATENT DOCUMENTS

| | | | |
|---|---|---|---|
| 4,468,390 | 8/1984 | Kitano | 424/232 |
| 4,661,489 | 4/1987 | Dorgan et al. | 514/211 |

FOREIGN PATENT DOCUMENTS

| | | |
|---|---|---|
| 0187012 | 9/1986 | European Pat. Off. |
| 0353959 | 7/1990 | European Pat. Off. |
| 8402571 | 7/1985 | South Africa |

OTHER PUBLICATIONS

Dialog record 1983677, Martindale ID: 2490–al–y, Dec. 1989.

*Primary Examiner*—Kimberly Jordan
*Attorney, Agent, or Firm*—Peter C. Richardson; Paul H. Ginsburg; Lorraine B. Ling

[57] ABSTRACT

Pharmaceutical compositions comprising a compound of formula (I) and at least one other anthelmintically active compound, being an avermectin or a milbemycin, are useful in the treatment of helminthiasis. In formula (I): R is optionally substituted phenyl, $C_{3-8}$ cycloalkyl, $C_{5-8}$ cycloalkenyl, $C_{1-8}$ straight or branched chain alkyl, $C_{2-8}$ straight or branched alkenyl, a 5- or 6-membered heterocyclyl, or optionally substituted phenyl $C_{1-4}$ alkyl; each of Y and Z, which may be the same or different, is oxygen or sulfur; and X is a bond, a methylene group (—$CH_2$—), or oxygen.

11 Claims, No Drawings

COMBINATIONS OF ANTHELMINTICALLY ACTIVE AGENTS

This application is a continuation of application No. 64,014, filed as PCT/GB91/01982 Jan. 7, 1994 published as WO92/08468 May 29, 1992, now abandoned.

The present invention relates to pharmaceutical compositions, in particular to compositions having broad spectrum anthelmintic activity, and their use in human and veterinary medicine.

The invention provides a pharmaceutical composition comprising a compound of formula (I):

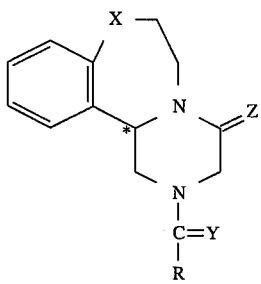

in which R is optionally substituted phenyl; $C_{3-8}$ cycloalkyl; $C_{5-8}$ cycloalkenyl; $C_{1-8}$ alkyl which may be straight or branched; $C_{2-8}$ alkenyl which may be straight or branched; 5- or 6- membered heterocyclyl; or optionally substituted phenyl $C_{1-4}$ alkyl, each of Y and Z, which may be the same or different, is oxygen or sulphur; and X is a bond, —$CH_2$—, or oxygen; and at least one other anthelmintically active compound which is a milbemycin.

Compounds of formula (I) wherein X is —$CH_2$— or oxygen, and processes for their production, are described in EP-A-0 134 984 and EP-A-0 187 012. An exemplary such compound is epsiprantel (2-(cyclohexylcarbonyl)-4-oxo-1, 2,3,4,6,7,8,12b-octahydropyrazino[2,1-a][2]benzazepine).

Compounds of formula (I) wherein X is a bond, and processes for their production, are described in DE-A-1 795 728, DE-A-24 41 261, DE-A-23 62 539 and by Andrews et al in Medicinal Research Reviews (John Wiley & Sons, Inc.) Vol.3, No. 2, 147–200 (1983). An exemplary such compound is praziquantel (2-cyclohexylcarbonyl [1,2,3,6,7,11b] hexahydro-4H-pyrazino[2,1-a]isoquinolin-4-one).

When used herein the term "pharmaceutical" includes the term "veterinary" and the term "pharmaceutically" includes the term "veterinarily".

Compounds of formula (I) have an asymmetric carbon atom marked by an asterisk in formula (I) and may therefore exist in at least two stereoisomeric forms. The present invention encompasses all isomers of the compounds of formula (I) whether pure or admixed with other isomers in any proportion.

When R is optionally substituted phenyl, it may be substituted with one or more moieties selected from halogen, $C_{1-6}$ alkyl, $C_{1-6}$ alkoxy, nitro, amino, mono-or-di-$C_{1-6}$ alkylamino, and hydroxy.

When R is heterocyclyl, it may be a 5 or 6-membered saturated or unsaturated group containing up to three heteroatoms selected from oxygen, sulphur and nitrogen. It will be appreciated that unsaturated heterocyclyl groups suitably include aromatic heterocyclyl groups.

The term "halogen" refers to fluorine, chlorine, bromine and iodine.

A preferred R group is cyclohexyl.

Compounds of formula (I) have anthelmintic activity especially against tapeworm such as *Taenia taeniaeformis* and *Dipylidium caninum*.

Suitable milbemycins for use in carrying out the present invention include compounds of partial formula (i)

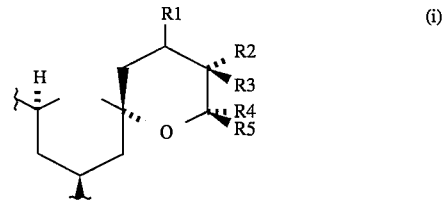

wherein $R^1$ is an optionally substituted amino or imino group such as optionally O-substituted oxyimino, optionally N-substituted hydrazone or optionally N-substituted semicarbazone, and $R^2$ to $R^5$ are the same or different and each is hydrogen or an organic radical.

Preferred compounds of formula (i) are compounds of formula (II):

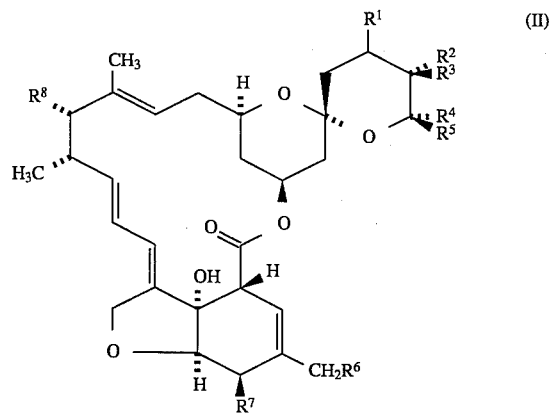

wherein $R^1$ to $R^5$ are as defined above, $R^6$ is hydrogen or optionally protected hydroxy; $R^7$ is alkoxy, optionally protected hydroxy, oxo or optionally O-substituted oxyimino; and $R^8$ is hydrogen, optionally protected hydroxy, or a group 4'- (α-L-oleandrosyl)-α-L-oleandrosyloxy or α-L-oleandrosyloxy wherein the terminal hydroxy group is optionally protected.

Compounds of formula (II), and processes for their preparation, are described in EP-A-0 259 779, EP-A-0 293 549, EP-A-0 307 225, GB-A-2 192 630, EP-A-0 260 536, EP-A-0 260 537, EP-A-0 307 220, and EP-A-0 421 568 (USSN 525,094).

Preferably, the compound of formula (II) is a compound in accordance with EP-A-0 421 568 more especially a compound wherein $R^1$ is O-substituted oxyimino, $R^2$ to $R^4$ are hydrogen, $R^5$ is an organic radical, $R^6$ and $R^8$ are hydrogen, and $R^7$ is hydroxy.

Suitable protecting groups for hydroxy include TBDMS (t-butyldimethylsilyl), and acyl. Further suitable protecting groups are described in, for example, "Protective Groups in Organic Synthesis" Theodora W. Greene, Wiley-Interscience 1981 Ch 2, 10–86.

When any of $R^2$ to $R^5$ is an organic radical it may advantageously be selected from the group consisting of alkyl, alkenyl, alkynyl, aryl, heterocyclyl, mono-, bi- and tri-cycloalkyl, mono-, bi- and tri-cycloalkenyl and aralkyl.

As used herein alkyl includes straight and branched $C_{1-20}$, more especially $C_{1-12}$, particularly $C_{1-6}$ alkyl, and alkenyl and alkynyl include straight and branched $C_{2-20}$, more especially $C_{2-12}$, particularly $C_{2-6}$ alkenyl and alkynyl.

When any of $R^2$ to $R^5$ comprises an alkyl, alkenyl or alkynyl moiety that moiety may optionally be substituted by one or more substituents selected from the group consisting of hydroxy, alkoxy, alkylthio, oxo, halogen, trifluoromethyl, and optionally substituted amino.

When used herein the term 'aryl' includes phenyl and naphthyl optionally substituted with up to five, preferably up to three, groups selected from halogen, $C_{1-6}$ alkyl, aryl, $C_{1-6}$ alkoxy, halo substituted $(C_{1-6})$ alkyl, hydroxy, amino, nitro, carboxy, $C_{1-6}$ alkoxycarbonyl, $C_{1-6}$ alkoxycarbonyl-$(C_{1-6})$-alkyl, $C_{1-6}$ alkylcarbonyloxy, or $C_{1-6}$ alkylcarbonyl groups.

The term 'heterocyclyl' includes saturated, unsaturated and aromatic single or fused rings comprising up to four hetero atoms in the ring selected from oxygen, nitrogen and sulphur and optionally substituted with up to three halogen, $C_{1-6}$ alkyl, $C_{1-6}$ alkoxy, halo- $(C_{1-6})$-alkyl, hydroxy, amino, carboxy, $C_{1-6}$ alkoxycarbonyl, $C_{1-6}$ alkoxycarbonyl$(C_{1-6})$ alkyl, aryl or oxo groups.

Suitably the heterocyclic ring comprises from 4 to 7 ring atoms, preferably 5 to 6 atoms.

The term 'halogen' refers to fluorine, chlorine, bromine and iodine.

Particularly suitable substituents for an amino or imino group such as an oxime, hydrazone or semicarbazone group include one or more organic radicals as defined hereinabove for $R^2$ to $R^5$, for example the substituents set out in EP-A-0 288 205, EP-A-0 259 779, EP-A-0 260 537, EP-A-0 260 536, GB-A-2 192 630, and EP-A-0 307 225.

Those skilled in the art will appreciate that an N-substituted imino group such as an oxime may exist as either an E or Z isomer, or as a mixture of E and Z isomers, and that an E or Z isomer may be converted to the other isomer or to a mixture of isomers by standard techniques such as acid treatment.

As used herein mono-, bi- and tri-cycloalkyl include $C_{3-20}$, especially $C_{3-12}$, more especially $C_{4-8}$, groups, and mono-, bi- and tri-cycloalkenyl include $C_{4-20}$, especially $C_{4-12}$, more especially $C_{5-8}$ groups. When any of $R^2$ to $R^5$ comprises a mono-, bi- or tri-cycloalkyl or mono-, bi- or tri-cycloalkenyl moiety, that moiety may be substituted as set out above for alkyl, alkenyl, and alkynyl, and/or by one or more substituents selected from the group consisting of methylene and alkyl. Bicyclic and tricyclic groups may be fused or bridged and are preferably attached via a carbon atom which is common to two rings.

Any two of $R^2$ to $R^5$ may be taken together with the carbon atom(s) to which they are attached to designate a cycloalkyl, cycloalkenyl, aryl or heterocyclyl group which may optionally be substituted as set out above.

The pharmaceutical composition of the invention is of use in the treatment of helminthiasis of the human or non-human animal body, and particularly for treating tapeworm and/or nematode infections of domestic animals and farm animals.

Accordingly, the present invention also provides a method of treating helminthiasis, particularly tapeworm and/or nematode infestations, in human or domestic animals, which method comprises administering to the human or domestic animal in need thereof an anthelmintically effective amount of a pharmaceutical composition of the invention.

Accordingly the present invention also provides a pharmaceutical composition, as hereinbefore defined, (hereinafter called "the composition") for use in the treatment of the human or non-human animal body, especially for treating helminthiasis and particularly for treating tapeworm and/or nematode infestations, of domestic animals, especially dogs and cats and farm animals.

Suitably, the composition comprises a pharmaceutically acceptable carrier; the particular carrier used depending upon the chosen means of administration.

Suitable carriers are those used conventionally in the art for the particular means of administration. Thus, for example, the composition may be a shaped composition, such as a bolus, tablet or capsule. In such cases the pharmaceutically acceptable carrier will be chosen from the usual range of lubricants, dispersants, binders, fillers and the like.

For administration to humans, especially children, the composition may suitably be presented as a syrup including suitable colouring and/or flavouring agents. Such syrups are conveniently presented in unit or multi-dose containers.

For veterinary use the composition may also be a dispersion or a solution of the composition in a suitable vehicle for use with an oral doser (this is a well known item of farm equipment, basically comprising a liquid reservoir, a mouthpiece adapted for insertion into animal mouths, and a pump mechanism whereby unit doses can be ejected from the reservoir through the mouthpiece). Conveniently the composition may be administered from an oral doser as an aqueous solution. Alternatively, the vehicle will be an oil or water based cream to ensure homogeneity of the unit doses administered.

The composition may also be added to the animal feed or drinking water. It will be convenient to formulate these animal feed and drinking water compositions with a multi-dose of the drug so that the animal takes in an appropriate quantity of the composition along with its diet. It will also be convenient to present the composition as a premix for addition to the feed or drinking water.

The composition may also be formulated for injection. In such cases the composition chosen is suitably dissolved or suspended in a suitable pharmaceutically acceptable vehicle, for example water propylene glycol or glycerol formal.

Suitably the composition comprises of sufficient material to provide a dose of from 0.01 to 250 mg of the compound of formula (I) per kg of animal body weight per dose, and from 0.001 to 100 mg of the milbemycin compound per kg of animal body weight per dose, more suitably 0.01 to 10mg/kg per dose.

The following Example illustrates the invention.

| Example | Dosage |
|---|---|
| Epsiprantel (prepared as described in Example 1 of EP-A-0 134 984) | 5 mg/kg animal body weight |
| VS 54936 (prepared as described in Example 6 of EP-A-0 421 568- Z isomer or mixture of E and Z isomers) | 0.1 mg/kg animal body weight |

I claim:

1. A pharmaceutical composition comprising a compound of formula (I):

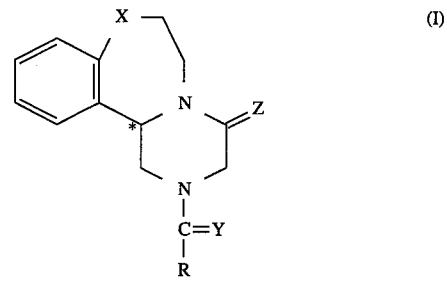

in which R is optionally substituted phenyl; $C_{3-8}$ cycloalkyl; $C_{5-8}$ cycloalkenyl; $C_{1-8}$ alkyl which may be straight or branched; $C_{2-8}$ alkenyl which may be straight or branched; a 5— or 6-membered heterocyclyl; or an optionally substituted phenyl $C_{1-4}$ alkyl, each of Y and Z, which may be the same or different, is oxygen or sulfur; and X is a bond, —$CH_2$—, or oxygen; and at least one other anthelmintically active compound which is an avermectin or milbemycin of partial formula (i):

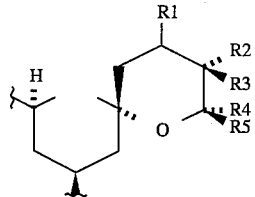
(i)

wherein $R^1$ is an optionally substituted amino or imino group and $R^2$ to $R^5$ are the same or different and each is hydrogen or an organic radical.

2. A composition according to claim 1, wherein X is —$CH_2$— or oxygen.

3. A composition according to claim 2, wherein the compound of formula (I) is epsiprantel.

4. A composition according to claim 1, wherein the compound of partial formula (i) is a compound of formula (II):

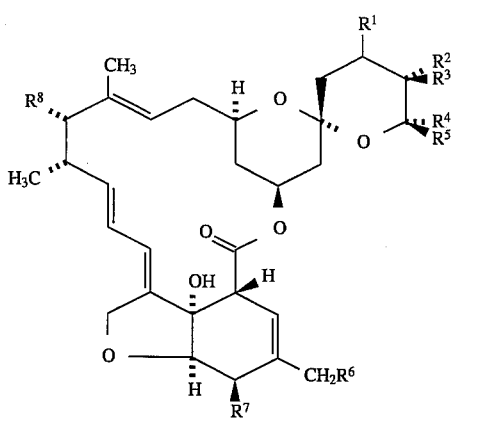
(II)

wherein $R^1$ to $R^5$ are as defined above, $R^6$ is hydrogen or optionally protected hydroxy; $R^7$ is alkoxy, optionally protected hydroxy, oxo or optionally O-substituted oxyimino; and $R^8$ is hydrogen, optionally protected hydroxy, or a group 4'-(α-L-oleandrosyl)-α-L-oleandrosyloxy or α-L-oleandrosyloxy wherein the terminal hydroxy group is optionally protected.

5. A composition according to claim 4, wherein the compound of formula (II) is a compound wherein $R^1$ is O-substituted oxyimino $R^2$ to $R^4$ are hydrogen, $R^5$ is an organic radical, $R^6$ and $R^8$ are hydrogen, and $R^7$ is hydroxy.

6. A composition according to claim 5, wherein the compound of formula (II) is the compound wherein $R^1$ is methoxyimino; $R^2$, $R^3$, $R^4$, $R^6$ and $R^8$ are hydrogen, $R^5$ is t-butyl, and $R^7$ is hydroxy:
in the form of the E or Z isomer or of a mixture of E and Z isomers.

7. A method of treating helminthiasis in human or domestic animals, which method comprises administering to the human or domestic animal in need thereof an anthelmintically effective amount of a pharmaceutical composition of claim 1.

8. A method according to claim 7, wherein the at least one other anthelmintically active compound is an avermectin or milbemycin compound according to claim 1.

9. A method according to claim 7, wherein the at least one other anthelmintically active compound is an avermectin or milbemycin compound according to claim 4.

10. A process for the preparation of a composition according to claim 1, which process comprises admixing (a) an amount of the compound of formula (I) effective to provide a dose of 0.01 to 250 mg thereof per kg of host animal body weight and (b) an amount of said at least one other anthelmintically active Compound effective to provide 0.001 to 100 mg thereof per kg of host animal body weight.

11. A composition according to claim 1, wherein $R^1$ is selected from the group consisting of optionally O-substituted oxyimino, optionally N-substituted hydrazone, and optionally N-substituted carbazone.

* * * * *